United States Patent [19]

Herzog et al.

[11] Patent Number: 4,812,568
[45] Date of Patent: Mar. 14, 1989

[54] PROCESS FOR THE PREPARATION OF 6,13-DIHYDROQUINACRIDONES AND QUINACRIDONES

[75] Inventors: Helmut Herzog, Leverkusen; Detlef-Ingo Schütze, Cologne; Jürgen Schneider; Reinold Schmitz, both of Odenthal, all of Fed. Rep. of Germany

[73] Assignee: Bayer Aktiengesellschaft, Leverkusen, Fed. Rep. of Germany

[21] Appl. No.: 12,921

[22] Filed: Feb. 10, 1987

[30] Foreign Application Priority Data

Feb. 25, 1986 [DE] Fed. Rep. of Germany ....... 3605976

[51] Int. Cl.$^4$ ............................................. C09B 48/00
[52] U.S. Cl. ........................................ 546/49; 546/56; 546/57
[58] Field of Search ............................ 546/49, 56, 57

[56] References Cited

U.S. PATENT DOCUMENTS

| 2,821,529 | 1/1958 | Struve | 546/49 |
| 2,969,366 | 1/1961 | Griswold et al. | 546/49 |
| 3,007,930 | 11/1961 | Manger et al. | 546/49 |
| 3,009,916 | 11/1961 | Struve | 546/49 |
| 3,738,988 | 6/1973 | Jackson | 546/49 |

FOREIGN PATENT DOCUMENTS

| 3605976 | 8/1987 | Fed. Rep. of Germany | 546/49 |
| 0051400 | 4/1977 | Japan | 546/49 |
| 0119532 | 9/1979 | Japan | 546/49 |
| 0057749 | 4/1982 | Japan | 546/56 |
| 1191409 | 5/1970 | United Kingdom . | |

OTHER PUBLICATIONS

Wunderlich et al., Chemical Abstracts, vol. 73:27081w (1970).
Condensed Chemical Dictionary, 6th ed., Reinhold Publishing Co., New York, (1961, p. 419, "Dowtherm" A).
Dictionary of Organic Compounds, vol. 3: Din–Iza, Oxford University Press, New York (1965), pp. 1280 and 1311.

Primary Examiner—Donald G. Daus
Assistant Examiner—Diana G. Rivers
Attorney, Agent, or Firm—Sprung Horn Kramer & Woods

[57] ABSTRACT

Process for the preparation of a 6,13-dihydroquinacridone of the general formula (I)

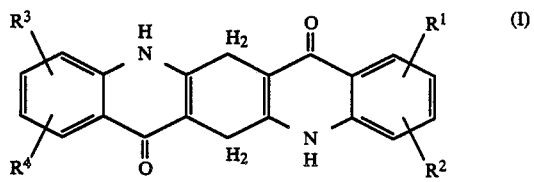

in which
$R^1$, $R^2$, $R^3$ and $R^4$ designate hydrogen or substituents customary for quinacridone, characterized in that an optionally substituted dialkyl 2,5-di-(phenylamino)-3,6-dihydroterephthalate is heated to temperatures of 240°–320° C. in an essentially oxygen-free atmosphere in the presence of a dimethyl-diphenyl ether isomer mixture of the formula

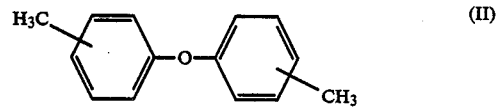

and/or

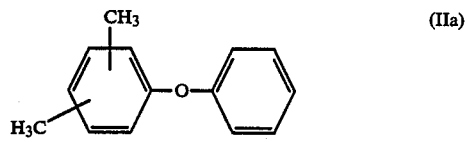

as the solvent and/or diluent, and a process for the preparation of optionally substituted quinacridone, characterized in that the resulting 6,13-dihydroquinacridone is oxidized in the customary manner.

8 Claims, No Drawings

PROCESS FOR THE PREPARATION OF 6,13-DIHYDROQUINACRIDONES AND QUINACRIDONES

The invention relates to a process for the preparation of a 6,13-dihydroquinacridone of the general formula (I)

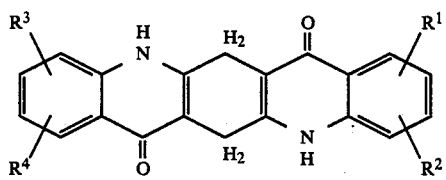

in which $R^1$, $R^2$, $R^3$ and $R^4$ designate hydrogen or substituents customary for quinacridone, characterized in that an optionally substituted dialkyl, preferably dimethyl or diethyl, 2,5-di-(phenylamino)-3,6-dihydroterephthate is heated to temperatures of 240°–320° C. in an essentially oxygen-free atmosphere in the presence of a dimethyldiphenyl ether isomer mixture of the formula (II) or (IIa) as the solvent and/or diluent.

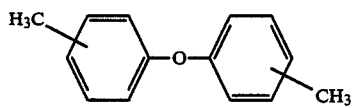

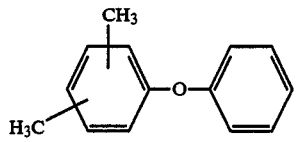

$R^1$, $R^2$, $R^3$ and $R^4$ preferably represent hydrogen, F, Cl, Br, I, —OH, —NO$_2$, —CF$_3$, an optionally substituted $C_1$-$C_4$-alkyl radical, an optionally substituted $C_1$-$C_4$-alkoxy radical, phenyl, cyclohexyl, phenoxy, —COOH, —COO— $C_1$-$C_4$-alkyl, —SO$_3$H,

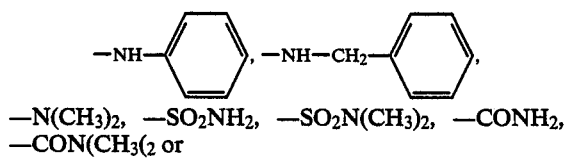

—N(CH$_3$)$_2$, —SO$_2$NH$_2$, —SO$_2$N(CH$_3$)$_2$, —CONH$_2$, —CON(CH$_3$)$_2$ or

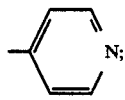

$R^1$ and $R^2$ (or $R^3$ and $R^4$) can also together form a fused-on benzo or naphtho ring.

Preferably, the isomer mixture (II), which can have, for example, the following composition, is employed: 0–5% by weight of 2,2'-dimethyldiphenyl ether, 5–40% by weight of 2,3'-dimethyldiphenyl ether, 5–30% by weight of 2,4'-dimethyldiphenyl ether, 10–50% by weight of 3,3'-dimethyldiphenyl ether, 10–50% by weight of 3,4'-dimethyldiphenyl ether, 0–20% by weight of 4,4'-dimethyldiphenyl ether and 0–5% by weight of other components.

A preferred composition for the isomer mixture is: 0–3% by weight of 2,2'-dimethyldiphenyl ether, 10–30% by weight of 2,3'-dimethyldiphenyl ether, 10–20% by weight of 2,4'-dimethyldiphenyl ether, 20–35% by weight of 3,3'-dimethyldiphenyl ether, 15–35% by weight of 3,4'-dimethyldiphenyl ether, 0–10% by weight of 4,4'-dimethyldiphenyl ether and 0–2% by weight of other components.

It is known from the literature that dialkyl 2,5-diarylamino-3,6-dihydro-terephthalates can be cyclized by means of high-boiling ethers in the temperature range from 240° to 300° C., the corresponding 6,13-dihydroquinacridones being obtained.

Thus, according to German Auslegeschrift No. 1,183,092, U.S. Pat. Nos. 2,821,529 and 2,821,530 and British Patent Specification No. 913,134, the use of a eutectic mixture of diphenyl and diphenyl ether ($\triangleq$ Dowtherm A) is proposed, whilst in Japanese Patent Specification No. 5,757,749 from Toyo Soda Mfg., the use of dibenzyl ether is recommended as the solvent.

However, these processes known from the literature cannot be satisfactory in terms of yield and quality.

We have now found, surprisingly, that 6,13-dihydroquinacridones (I) are formed in an excellent yield and high purity by the process of the invention; they serve as useful intermediate products for the synthesis of quinacridone pigments.

The dialkyl 2,5-di-(phenylamino)-3,6-dihydro-terephthalates used as starting compounds are known compounds, synthesis of which is possible from commercially available intermediate products.

The condensation of the aniline or derivatives thereof with dialkylsuccinyl succinate, if appropriate in the presence of a solvent, at elevated temperature and if appropriate under pressure, is acid-catalysed, examples of acids which can be used being aniline salts, HCl, H$_2$SO$_4$, acetic acid and p-toluenesulphonic acid.

Solvents which are used are, for example, alcohols, such as methanol or ethanol, toluene, xylene or the dimethylphenyl ether isomer mixture (II).

If appropriate, the (substituted) aniline can simultaneously serve as the reaction component and solvent, especially if it is used in a large excess.

Depending on the solvents, it may be beneficial for the water of reaction formed during the condensation to be removed by distillation, for example using a water separator or in vacuo.

The anilines used are, for example, aniline, m- and p-chloroaniline, m- and p-toluidine and p-anisidine, m- and p-fluoroaniline, m- and p-bromoaniline, m- and p-nitroaniline, m- and p-trifluoromethylaniline, 4-ethylaniline, 4-cyclohexylaniline, sulphanilic acid, 4-aminobenzoic acid, methyl 4-aminobenzoate, 4-phenylaniline, 3,4- or 3,5-dichloroaniline and 3,4- or 3,5-dimethylaniline; aniline is particularly preferred.

The use of dimethyl 2,5-dianilino-3,6-dihydro-terephthalate as the starting material for the cyclization is a particularly preferred process variant according to the invention.

A suitable solvent and/or diluent is the dimethyl phenyl ether isomer mixture of the general formula (II).

The conversion of the dialkyl 2,5-diphenylamino-3,6-dihydro-terephthalates into the corresponding 6,13-dihydroquinacridones in the presence of an isomer mixture of the formula (II) or (IIa) is effected in the temperature range from 240° to 320° C., preferably at 280°–290° C., under an inert gas atmosphere, it being possible to use, for example, nitrogen, carbon dioxide and argon as the inert gas.

A preferred embodiment of the process according to the invention comprises metering a hot suspension, at 100°–150° C., of dimethyl or diethyl 2,5-dianilino-3,6-dihydro-terephthalate and the isomer mixture (II) or (IIa) into the boiling isomer mixture (II) or (IIa) under nitrogen in the course of 15–90 minutes and bringing the cyclization to completion by heating the mixture under reflux for 15–60 minutes, methanol or ethanol being distilled off.

Preferably, 3–20 parts by volume, and particularly preferably 5–12 parts by volume, of the isomer mixture (II) or (IIa) are employed per part by weight of 2,5-dianilinodihydro diester.

The preparation of the unsubstituted 2,5-dianilino-3,6-dihydro dialkyl esters and the subsequent cyclization to give the 6,13-dihydroquinacridone in the isomer mixture (II) or (IIa) can advantageously also be carried out as a one-pot reaction.

For this reason, for example, succinylosuccinic acid dialkyl esters are condensed with at least 2 mol, preferably 4–8 mol, of aniline in the isomer mixture (II) or (IIa), as the solvent and/or diluent, in the presence of an acid catalyst, preferably aqueous hydrochloric acid, at 90°–130° C. under 20–120 mbar and the mixture is then neutralized with aqueous sodium carbonate solution.

The reaction mixture is subsequently freed from water and excess aniline by vacuum distillation and, if appropriate, is diluted with the isomer mixture (II) or (IIa).

The suspension consisting of the dialkyl 2,5-dianiline-3,6-dihydro-terephthalate and the isomer mixture (II) or (IIa) is then cyclized to give the 6,13-dihydroquinacridone, as described above.

After cyclization in the isomer mixture (II) or (IIa), a suspension of the optionally substituted 6,13-dihydroquinacridone in the isomer mixture is obtained and is worked up in the customary manner. For example, the product can be filtered off with suction at temperatures <150° C. and the suction filter cake obtained can be freed from adhering solvents and by-products by washing with alcohol, preferably methanol, and, if appropriate, can then be extracted by stirring again in hot methanol, in order to remove residues of the isomer mixture (II) or (IIa).

During working up, the one-pot process also requires, in addition to the alcohol wash, washing with water to remove salts contained in the product.

All the waste products obtained in the cyclization process (mother liquors, wash liquors) can be worked up by distillation without problems to give a high yield of the isomer mixture (II) or (IIa) and methanol, whilst the residues are burned in liquid form.

The synthesis of the optionally substituted 6,13-dihyroquinacridones starting from dialkyl 2,5-dianilino-3,6-dihydroterephthalates by a cyclization reaction in the isomer mixture (II) or (IIa) proceeds with a high yield.

The isomer mixture (II) is preferably employed in all the abovementioned reactions.

High yields are likewise obtained for the one-pot process, starting from substituted succinylsuccinic acid dialkyl esters.

The products prepared according to the invention are obtained in a very pure form, as shown by the IR and UV spectroscopy data; they can be further processed as methanol-containing or aqueous pastes or in the dry form.

The oxidation of 6,13-dihydroquinacridones is known in principle (for example according to U.S. Pat. No. 2,821,529, Examples 9–15; British Patent Specification No. 909,602, Examples 1–6; and British Patent Specification No. 911,477, Examples 1–11).

The compounds of the general formula (I) synthesized by the process of the invention can be converted into the corresponding quinacridones, for example by oxidation by means of sodium m-nitrobenzenesulphonate, nitrobenzene, nitronaphthalene, nitrobenzenesulphonic acid and -carboxylic acid, nitrophenols, oxygen or air, in solvent mixtures of methanol, ethanol, acetone or ethylene glycol or glycol ethers and water in the presence of an alkali at elevated temperature and if appropriate under pressure, and if appropriate in the presence of dispersing agents and reaction accelerators. The oxidation is preferably carried out with air in the presence of a dispersing agent, preferably an anionic dispersing agent, for example a condensation product of an aromatic sulphonic acid and formaldehyde.

Isolation of the deep red-coloured quinacridones is usually effected by filtration, followed by washing with alcohol (if appropriate) and water. After drying, the crude pigment may have to be converted into an optimum finely divided form by suitable finishing (for example salt grinding).

According to the invention, for example, the following quinacridones can be synthesized: $\beta$- and $\gamma$-quinacridone, 2,9-dichloroquinacridone, 3,10-dichloroquinacridone, 2,9-dimethylquinacridone, 2,9-dimethoxyquinacridone, 2,9-diethoxyquinacridone, 2,4,9,11-tetrachloroquinacridone, 2,9-dicyclohexylquinacridone, 2,9-diphenylquinacridone, 3,10-dinitroquinacridone, 1,2,8,9-tetrachloroquinacridone, 2,9-difluoroquinacridone, and 2,9-dibromoquinacridone.

The invention furthermore relates to a process for the preparation of $\gamma$-quinacridone, which is characterized in that the 6,13-dihydroquinacridone obtained by the processes described above is treated with a substantially anhydrous mixture of a $C_1$–$C_4$-alcohol and an alkali and the dihydroquinacridone is subsequently oxidized in the customary manner, preferably with air, as described above. Preferably, 3–10, preferably 4–6, parts by weight of alcohol, 0.3–1, preferably 0.3–0.6, part by weight of alkali and 0–0.5, preferably 0–0.1, parts by weight of water are employed per part by weight of 6,13-dihydroquinacridone. Methanol is preferably used as the alcohol. Sodium hydroxide is preferably used as the alkali.

The treatment of the 6,13-dihydro compound can be carried out, for example, by heating the reaction mixture at the boiling point for 15–60 minutes or stirring it at room temperature for several hours.

A conversion of $\alpha$- into $\beta$-6,13-dihydroquinacridone is as a rule effected by the treatment with the alcohol/alkali mixture. The $\gamma$-quinacridone obtained by the new process is distinguished by a high purity, a high covering power, a high gloss and other outstanding coloristic properties.

The process according to the invention may be illustrated in more detail with the aid of the examples which now follow.

EXAMPLE 1

A mixture of 600 ml of methanol, 34.3 ml of glacial acetic acid, 95.9 ml of aniline and 100 g of dimethyl succinylsuccinate is heated to 100° C. in a 1.2 l VA autoclave in the course of 30 minutes and is kept at 100°–105° C. for 6 hours.

After cooling, the autoclave is let down and a sample, which according to thin layer chromatography contains <3% of starting material, is taken from the reaction mixture.

The resulting suspension is filtered with suction and the residue is washed successively with methanol and water and dried at 70°–80° C. in vacuo. 160 g ≙ effectively 96.5% of a product which is pale orange-red in colour, is 96–98% pure according to HFC, has a characteristic IR spectrum and is represented by formula (III) are obtained:

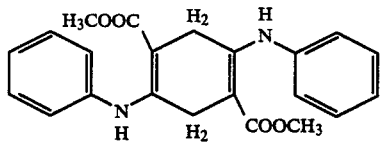

(1a) If aniline is replaced by 134 g of p-chloro- or m-chloroaniline and the procedure is otherwise as described above, effective yields of 96.7% ≙ 189.5 g and 95.5% ≙ 186.2 g of products which contain 15.95% and 15.7% of chlorine respectively, have characteristic IR spectra and correspond to the formulae (IV) and (V) are obtained:

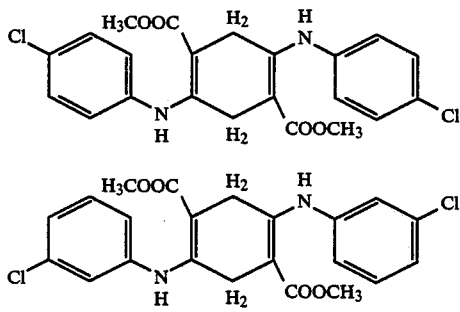

(1b) If aniline is replaced by 112.4 g of p-toluidine and the procedure followed is otherwise as described in Example 1, 173.4 g=effectively 97.3% of a compound which has characteristic IR bands and corresponds to the following formula are obtained:

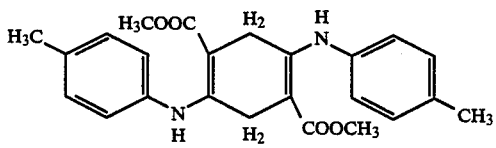

EXAMPLE 2

A suspension of 80 g of dimethyl 2,5-dianilino-3,6-dihydro-terephthalate, prepared according to Example 1, in 350 ml of a mixture of <3% by weight of 2,2'-, 10–30% by weight of 2,3'-, 10–20% by weight of 2,4'-, 20–35% by weight of 3,3'-, 15–35% by weight of 3,4'- and <10% by weight of 4,4'-dimethyldiphenyl ether is heated to 100°–105° C. in a 1 l beaker with a ground glass flange and a bottom outlet valve, with stirring ($N_2$ atmosphere).

This hot suspension is then metered into 450 ml of boiling isomer mixture of the composition described in the preceding paragraph (temperature: 280°–290° C., stirrer speed: 200 revolutions/minute) under $N_2$ in the course of 45–60 minutes and the reaction mixture is subsequently kept at 284°–7° C. (reflux) for a further 20–30 minutes.

The reaction already starts after a few minutes, with evolution of methanol (a total of about 15–16 ml of methanol containing dimethyldiphenyl ether are obtained by distillation), associated with the onset of the formation of dihydroquinacridone in the form of an orange-coloured precipitate (severe foaming).

After cooling to 20°–30° C., the resulting suspension is filtered off with high suction over a 11-G3 glass suction filter and washed 5 times with 100 ml of methanol each time, after which the runnings are still slightly yellow in colour.

The suction filter cake is then heated briefly as the boiling point with 400 ml of methanol, with thorough stirring, and is filtered off with suction, washed with about 300 ml of methanol until the runnings are colourless and dried at 70°–80° C. in vacuo.

62.5 g ≙ effectively 94.1% of pale pink-coloured 6,13-dihydroquinacridone of the formula (VI)

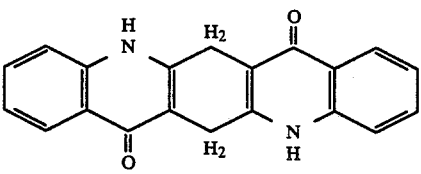

which, according to the IR and UV spectra, is very pure, are obtained.

(2a) If the amount of isomer mixture is reduced to 600 ml (=7.5 parts by volume per part by weight of dimethyl 2,5-dianilino-3,6-dihydro-terephthalate) and the procedure followed is otherwise as described above, the yield of pure 6,13-dihydroquinacridone is 60.9 g=effectively 91.6%.

EXAMPLE 3

A reaction mixture of 50 g of dimethyl succinylsuccinate (=DMSS), 250 ml of the dimethyldiphenyl ether isomer mixture described in Example 1, 150 ml of aniline and 0.5 ml of 30% strength hydrochloric acid is first stirred at 20°–30° C. for about 30 minutes and is then warmed to 105°–110° C. in the course of 1 hour, with thorough stirring and under a vacuum of 70 mm Hg. The mixture is then kept at 105°–110° C. for 3 hours, 9–12 ml of a water/aniline mixture being distilled off. After this time, virtually no further DMSS can be detected by thin layer chromatography.

After cooling to 50° C., the mixture is aerated and 0.3 g of anhydrous sodium carbonate, dissolved in 10 ml of water, is added, under nitrogen, and the mixture is stirred at 50°–60° C. for 1 hour.

170 ml of a water/aniline/dimethylphenyl ether isomer mixture are subsequently distilled off under a waterpump vacuum of 15–30 mm Hg; the reaction suspension, consisting of dimethyl 2,5-dianilino-3,6-dihydro-terephthalate and isomer mixture, is virtually free from aniline.

After cooling and aerating, the reaction mixture is diluted with 200 ml of the dimethyldiphenyl ether isomer mixture and is heated to 100°–150° C., under nitrogen and with thorough stirring, the hot suspension is metered into 600 ml of boiling isomer mixture in the course of 45-60 minutes, under N₂, and the mixture is then kept at 284°-7° C. for a further 20-30 minutes (reflux).

Working up is completed as was described in Example 2, the product additionally also being washed with water before drying.

60.5 g=effectively 87.8% (based on the DMSS employed) of pure 6,13-dihydroquinacridone (VI) are obtained.

EXAMPLE 4

If the procedure followed is as described in Example 2, but the compound (IV) prepared according to Example 1a is used as the starting material, 63 g=effectively 91.9% of pure 2,9-dichloro-6,13-dihydroquinacridone of the formula (VII) are obtained

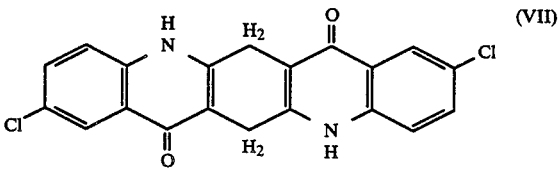

EXAMPLE 4a

If the procedure followed is as according to Example 2, but the product synthesized according to Example 1b is employed, 59.6 g=effectively 88.4% of pure 2,9-dimethyl-6,13-dihydroquinacridone of the formula (VIII) are obtained

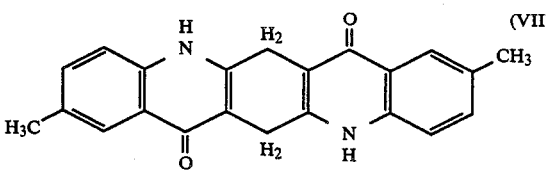

EXAMPLE 5

12 g of NaOH rotuli are dissolved with thorough stirring in 140 ml of methanol in 1 l beaker with a ground glass flange and an anchor stirrer, and 30 g of 6,13-dihydroquinacridone, prepared according to Example 2, are then introduced.

After dilution with 60 ml of methanol, the mixture is subsequently stirred at 20°-30° C. for 10 minutes and is then heated under reflux by means of an oil bath for 1 hour.

A hot solution, at 65° C., of 3 g of a commercially available dispersing agent, for example based on a condensation product of an aromatic sulphonic acid and formaldehyde, in 220 ml of distilled water is now added and the mixture is warmed under reflux for a further 30 minutes.

After addition of 0.75 g of sodium anthraquinone-2-sulphonate, the mixture is subsequently heated under reflux (70°-80° C.) for 10-15 hours and 10-15 l of air/hour are passed through the suspension via a rotameter, the colour gradually changing from pale pink to deep red.

The progress of the reaction is monitored by UV spectroscopy by taking samples.

When the reaction is complete, the mixture is filtered hot with suction over a ½ l G4 frit and the suction filter cake is washed neutral with hot water until the runnings are colourless.

The suction filter cake is then beaten into 400 ml of distilled water and the mixture is rendered acid to Congo red with approximately 1.5 ml of 50% strength sulphuric acid and stirred at about 80° C. for approximately 30 minutes.

After filtration with suction, the filter cake is washed neutral with hot distilled water and dried at 60°-80° C.

29 g=effectively 97.3% of pure γ-quinacridone pigment which, in a lacquer coating, gives a deep red with a high covering powder, a high gloss, a high clarity and very good flow properties, are obtained.

EXAMPLE 6

A mixture of 240 ml of methanol and 60 g of NaOH is stirred until almost all the solids have dissolved.

After introduction of 30 g of 6,13-dihydroquinacridone, prepared according to Example 2, the mixture is diluted with a solution of 3 g of a commercially available dispersing agent in 180 ml of water and is then subsequently stirred at 20°-30° C. for a further 30 minutes.

The mixture is subsequently heated under reflux for 10-15 hours, while passing in 10-15 l of air/hour, the progress of the reaction being monitored by UV spectroscopy by removing samples.

When the reaction is complete, the mixture is diluted with 500 ml of warm water, at 60°-65° C., at the boiling point and is subsequently stirred at 65°-70° C. for a further hour.

The resulting suspension is filtered with suction and the surface filter cake is washed neutral with hot water and dried at 70°-80° C. in vacuo.

28 g ≙ effectively 93.9% of a product which, after finishing, for example after salt grinding, can be converted into highly pure glazing or covering β-quinacridone pigments (shade: violet) are obtained.

EXAMPLE 7

A mixture of 155 ml of methanol, 65 ml of water and 24.8 g of potassium hydroxide is dissolved at 50°-60° C. with stirring, and 27.5 g of 2,9-dichlorodihydroquinacridone, prepared according to Example 4, are then introduced at 20°-30° C. in the course of about 15 minutes.

The reaction mixture is then warmed to 40°-50° C. and is brought together with 35.8 g of sodium m-nitrobenzenesulphonate into a 0.7 l VA autoclave, and is subsequently heated at 100° C. for 5 hours.

A sample taken after this time and worked up contains <5% of starting material, according to UV spectroscopy. When the reaction is complete, the autoclave is let down and emptied, 300 ml of distilled water are added to the mixture and the resulting suspension is subsequently stirred at −65° C. for a further 30 minutes.

The mixture is now filtered hot with suction and the residue is washed neutral with hot distilled water until the runnings are colourless and dried at 70° C. in vacuo. 25.5 g=effectively 93.2% of a compound which, after finishing, for example salt grinding, can be converted into highly pure glazing or covering magenta-coloured 2,9-dichloroquinacridone pigments are obtained.

EXAMPLE 8

A mixture consisting of 22 g of KOH/45 ml of distilled water (solution), 24.6 g of 2,9-dimethyldihydroquinacridone, prepared according to Example 4a, and 38 g of sodium m-nitrobenzenesulphonate is introduced into a 0.7 l VA autoclave and heated at 100°–105° C. for 8 hours.

After this time, the oxidation is virtually concluded, as can be demonstrated by UV spectroscopy.

Working up according to Example 7 leads to a product (23.8 g=effectively 97.3%), which, by finishing, for example by means of salt grinding, can be converted into highly pure glazing or covering bluish-tinged red 2,9-dimethylquinacridone pigments.

We claim:

1. A process for the preparation of γ-quinacridone which comprises heating a dialkyl 2,5-di-(phenylamino)-3,6-dihydroterephthalate at 280°–290° C. in an essentially oxygen-free atmosphere in the presence of a solvent comprising a dimethyldiphenyl ether isomer mixture of the formula

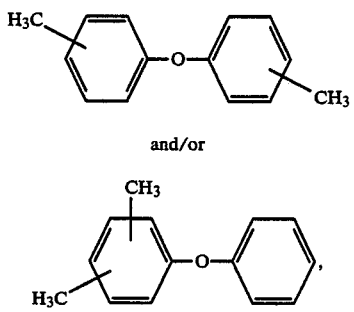

and/or thereby to produce 6,13-dihydroquinacridone, treating the 6,13-dihydroquinacridone with a substantially anhydrous mixture of a $C_1$–$C_4$-alcohol and an alkali, and oxidizing 6,13-dihydroquinacridone thereby to produce the γ-quinacridone.

2. The process according to claim 1, wherein the treatment of the 6,13-dihydroquinacridone is effected with a mixture of methanol and NaOH.

3. The process according to claim 2, wherein the oxidation of the 6,13-dihydroquinacridone is effected with air.

4. The process according to claim 1, wherein the solvent in which the dialkyl 2,5-di-(phenylamino)-3,6-dihydroterephthalate is heated is an isomer mixture of 0–5% by weight of 2,2'-dimethyldiphenyl ether, 5–40% by weight of 2,3'-dimethyldiphenyl ether, 5–30% by weight of 2,4'-dimethyldiphenyl ether, 10–50% by weight of 3,3'-dimethyldiphenyl ether, 10–50% by weight of 3,4'-dimethyldiphenyl ether, 0–20% by weight of 4,4'-dimethyldiphenyl ether and 0–5% by weight of other components.

5. The process according to claim 1, wherein the solvent in which the dialkyl 2,5-di-(phenylamino)-3,6-dihydroterephthalate is heated is an isomer mixture of 0–30% by weight of 2,2'-dimethyldiphenyl ether, 10–30% by weight of 2,3'-dimethyldiphenyl ether, 10–20% by weight of 2,4'-dimethyldiphenyl ether, 20–35% by weight of 3,3'-dimethyldiphenyl ether, 15–35% by weight of 3,4'-dimethyldiphenyl ether, 0–10% by weight of 4,4'-dimethyldiphenyl ether and 0–20% by weight of other components.

6. The process according to claim 1, wherein the dihydroterephthalate is dimethyl or diethyl 2,5-di-(phenylamino)-3,6-dihydroterephthalate.

7. The process according to claim 1, wherein 3–20 parts by volume of the isomer mixture are employed per part by weight of the dialkyl 2,5-di-(phenylamino)-3,6-dihydroterephthalate.

8. The process according to claim 1, wherein 5–12 parts by volume of the isomer mixture are employed per part by weight of the dialkyl 2,5-di-(phenylamino)-3,6-dihydroterephthalate.

* * * * *

UNITED STATES PATENT AND TRADEMARK OFFICE
CERTIFICATE OF CORRECTION

PATENT NO. : 4,812,568
DATED : March 14, 1989
INVENTOR(S) : Herzog et al

It is certified that error appears in the above-identified patent and that said Letters Patent is hereby corrected as shown below:

Col. 6, line 17       Delete "as" and substitute --at--

Col. 8, line 42       Delete "65" and substitute --45--

Signed and Sealed this

Twenty-seventh Day of March, 1990

Attest:

JEFFREY M. SAMUELS

Attesting Officer          Acting Commissioner of Patents and Trademarks